United States Patent
Konno et al.

(10) Patent No.: US 11,089,957 B2
(45) Date of Patent: Aug. 17, 2021

(54) SENSOR

(71) Applicant: NIHON KOHDEN CORPORATION, Tokyo (JP)

(72) Inventors: Norihito Konno, Tokyo (JP); Hirohiko Ikeya, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 16/098,362

(22) PCT Filed: Jun. 13, 2017

(86) PCT No.: PCT/JP2017/021764
§ 371 (c)(1),
(2) Date: Nov. 1, 2018

(87) PCT Pub. No.: WO2018/003487
PCT Pub. Date: Jan. 4, 2018

(65) Prior Publication Data
US 2019/0117067 A1   Apr. 25, 2019

(30) Foreign Application Priority Data

Jun. 28, 2016  (JP) .............................. JP2016-127896

(51) Int. Cl.
*A61B 5/00* (2006.01)
*A61B 5/117* (2016.01)
(Continued)

(52) U.S. Cl.
CPC ............ *A61B 5/0002* (2013.01); *A61B 5/002* (2013.01); *A61B 5/117* (2013.01); *A61B 5/0816* (2013.01);
(Continued)

(58) Field of Classification Search
None
See application file for complete search history.

(56) References Cited

U.S. PATENT DOCUMENTS 8,558,933 B2   10/2013 Sakai
2010/0315225 A1*  12/2010 Teague .................. A61B 5/002
340/539.12
(Continued)

FOREIGN PATENT DOCUMENTS

CN       102149318 A      8/2011
CN       102791189 A     11/2012
(Continued)

OTHER PUBLICATIONS

International Search Report issued in Patent Application No. PCT/JP2017/021764 dated Aug. 30, 2017.
(Continued)

*Primary Examiner* — Curtis A Kuntz
*Assistant Examiner* — Jerold B Murphy
(74) *Attorney, Agent, or Firm* — Pearne & Gordon LLP

(57) ABSTRACT

A sensor (1) including: an acquisition unit (11) which can acquire patient identification information so that a patient can be identified by the acquired patient identification information; a storage unit (12) which stores the patient identification information acquired by the acquisition unit (11); a detection unit (13) which can detect vital information of the patient; an association unit (14) which associates the patient identification information stored in the storage unit (12), with the vital information; and a transmission unit (15) which can transmit the vital information including the associated patient identification information, to a bedside monitor.

8 Claims, 4 Drawing Sheets

(51) Int. Cl.
*G16H 10/60* (2018.01)
*A61B 5/08* (2006.01)
*A61B 5/1455* (2006.01)
*A61B 5/318* (2021.01)

(52) U.S. Cl.
CPC .......... *A61B 5/14551* (2013.01); *A61B 5/318* (2021.01); *A61B 2562/08* (2013.01); *G16H 10/60* (2018.01)

(56) References Cited

U.S. PATENT DOCUMENTS

| | | | |
|---|---|---|---|
| 2011/0166491 A1 | 7/2011 | Sankai | |
| 2011/0175735 A1 | 7/2011 | Forster | |
| 2011/0221590 A1* | 9/2011 | Baker | G16H 40/63 |
| | | | 340/539.12 |
| 2012/0003933 A1 | 1/2012 | Baker et al. | |
| 2013/0120157 A1* | 5/2013 | Geva | A61F 13/0246 |
| | | | 340/870.16 |
| 2013/0331036 A1* | 12/2013 | Baker | G06F 19/3418 |
| | | | 455/41.3 |
| 2014/0379369 A1* | 12/2014 | Kokovidis | A61B 5/002 |
| | | | 705/2 |
| 2017/0147772 A1* | 5/2017 | Meehan | G16H 40/63 |

FOREIGN PATENT DOCUMENTS

| | | |
|---|---|---|
| CN | 102844000 A | 12/2012 |
| JP | 2010-069193 A | 4/2010 |
| JP | 2013-517042 A | 5/2013 |
| WO | 2011-062558 A1 | 5/2011 |
| WO | 2011-083453 A1 | 7/2011 |
| WO | 2013-103342 A1 | 7/2013 |

OTHER PUBLICATIONS

Written Opinion issued in Patent Application No. PCT/JP2017/021764 dated Aug. 30, 2017.

Japanese Office Action issued in Japanese Patent Application No. 2016-127896-A dated Jun. 2, 2020.

Chinese Office Action dated Mar. 2, 2021 issued in Patent Application No. 201780040646.4.

\* cited by examiner

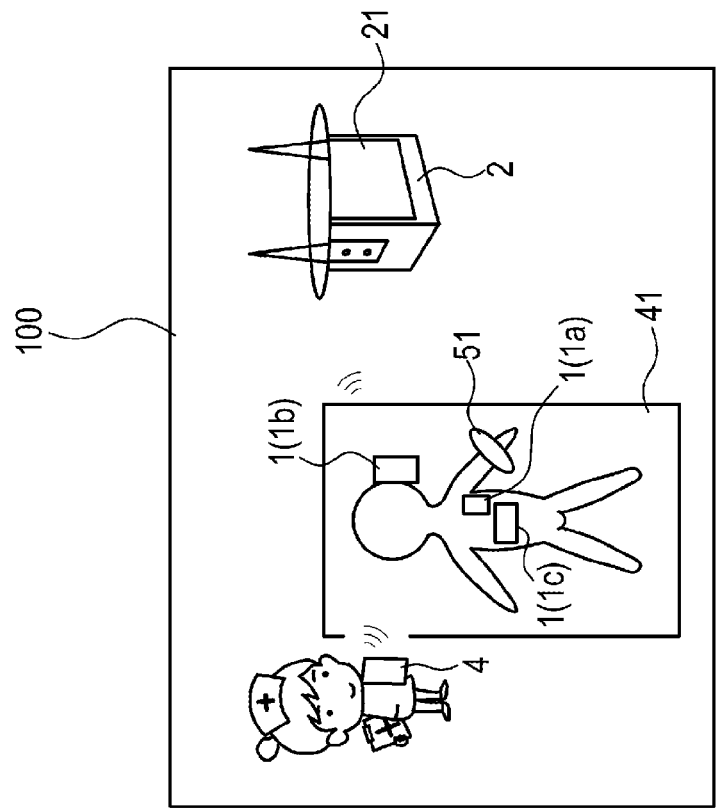
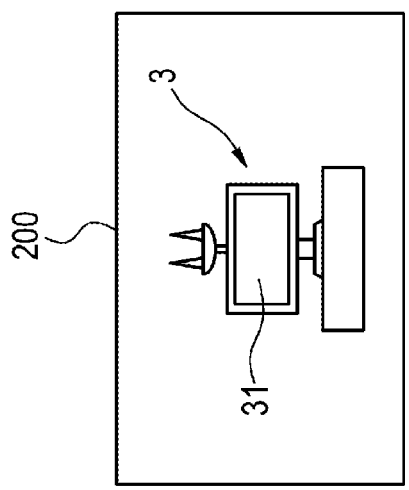
[Fig. 1]

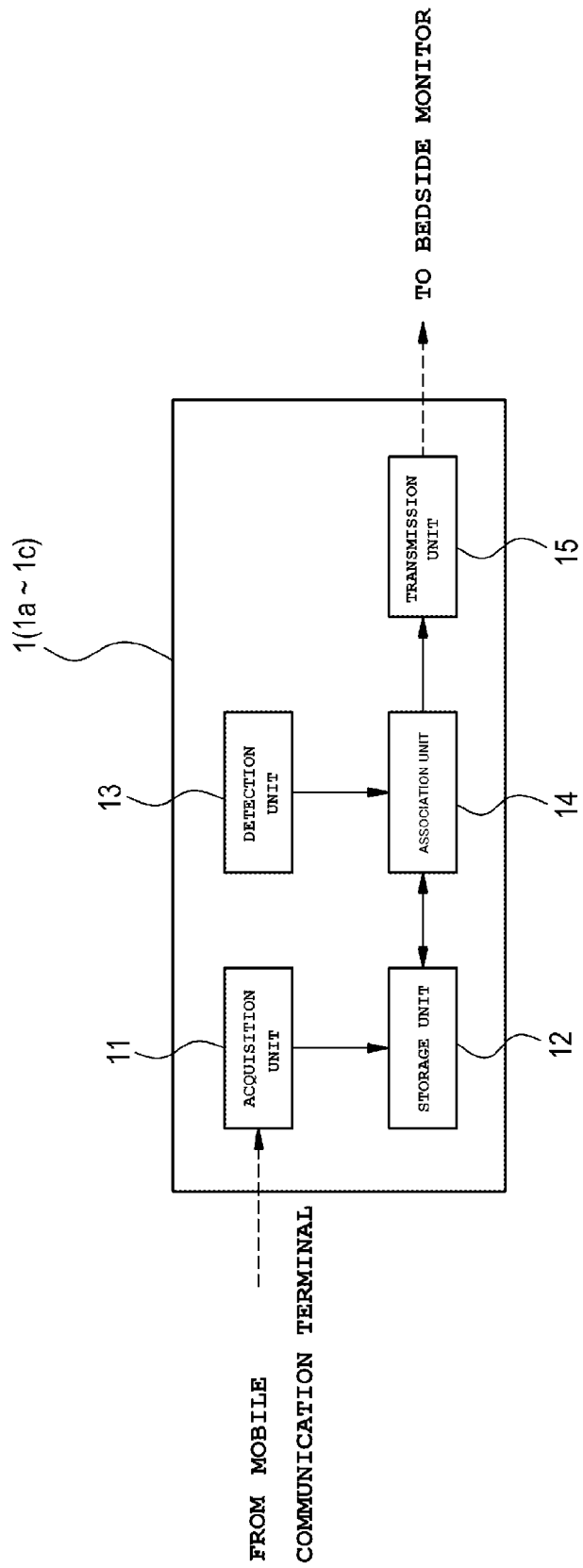

[Fig. 3]
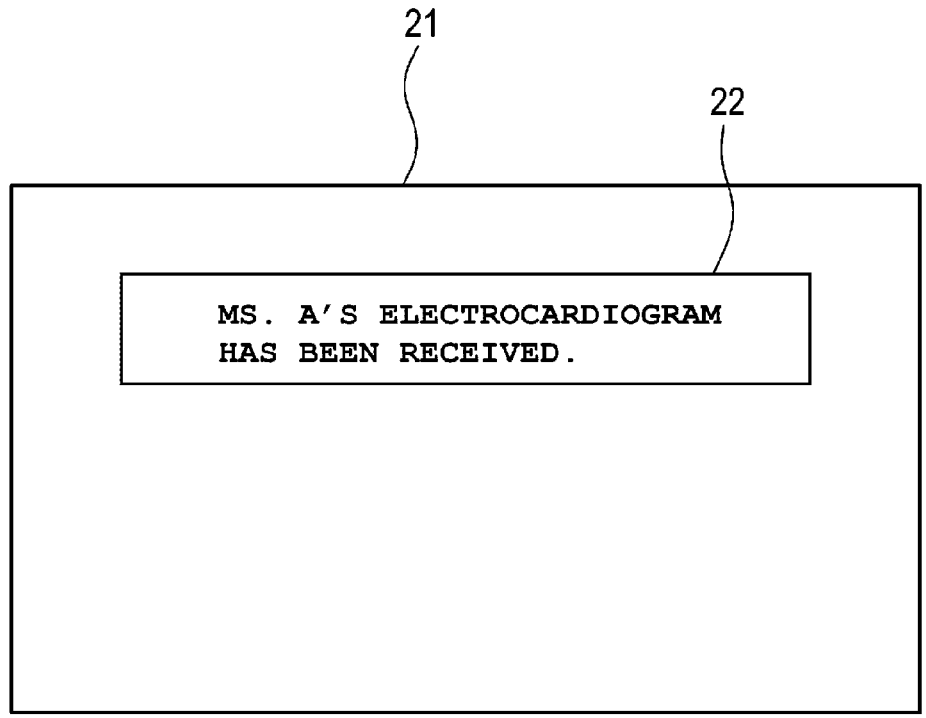
[Fig. 4]
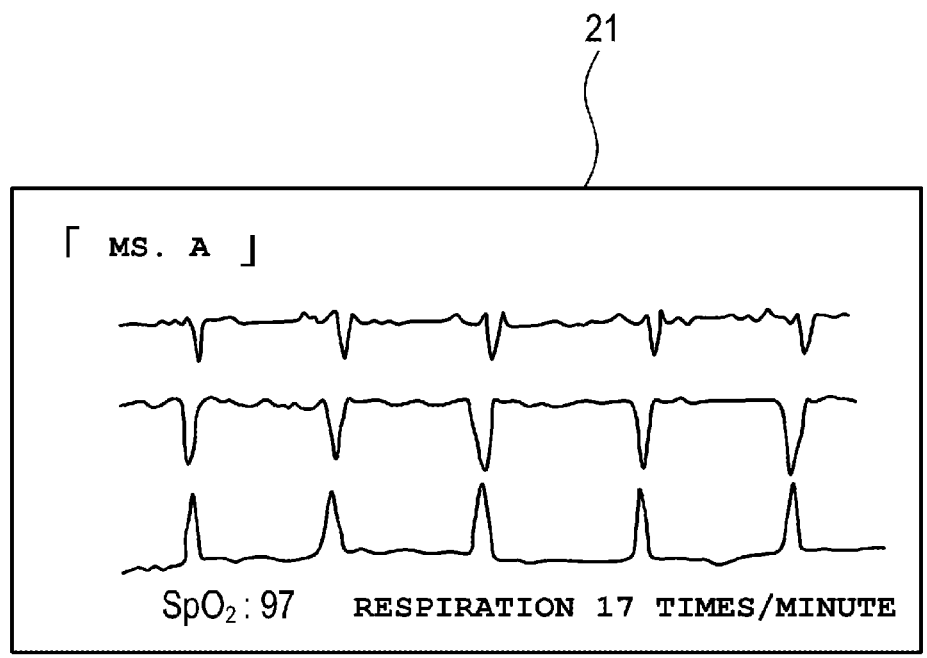

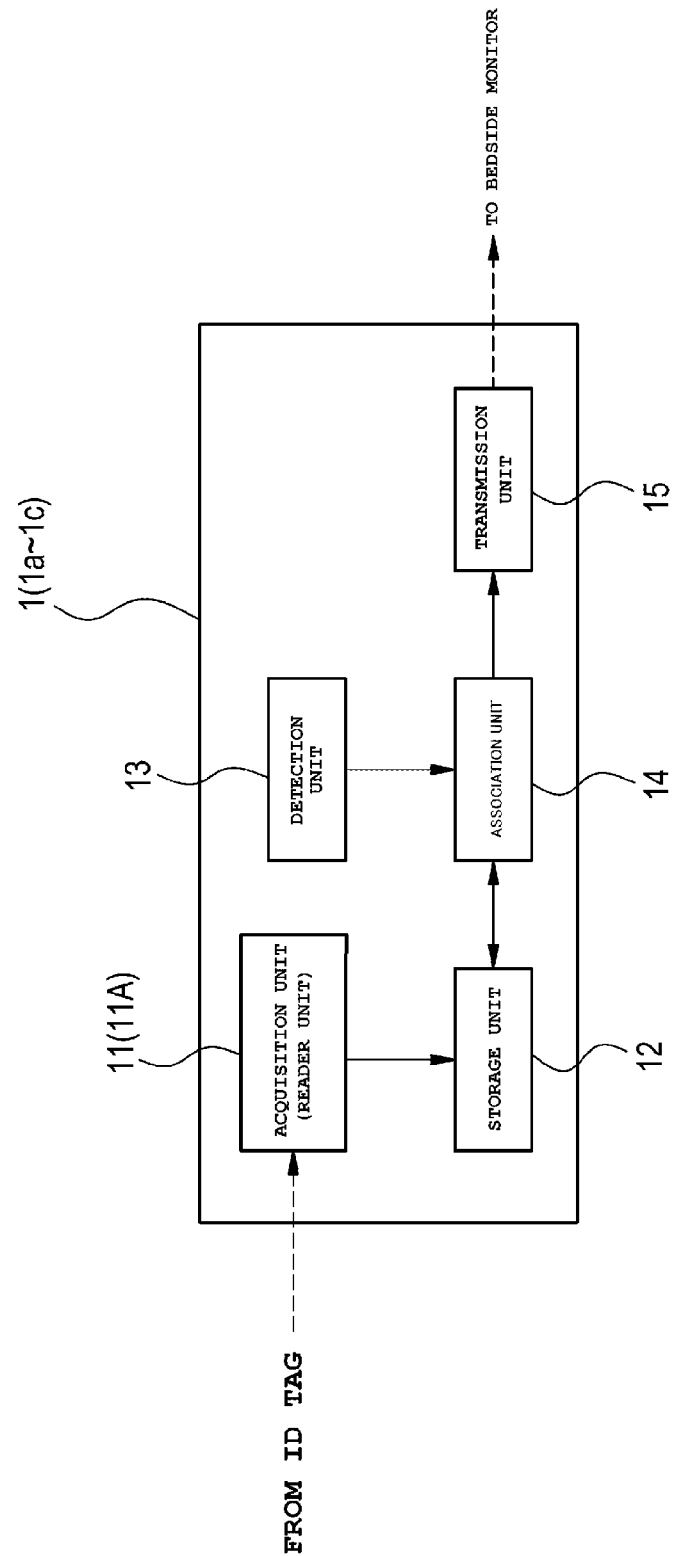

SENSOR

TECHNICAL FIELD

The present invention relates to a sensor for acquiring information from an object.

BACKGROUND ART

Assume that a sensor which is attached to a patient is connected to a display device by a cable (wire). In such a configuration, movement of the patent may be restricted by the cable. To solve this problem, for example, there is a system having a configuration in which a sensor can communicate with a display device by wireless (see Patent Literature 1).

CITATION LIST

Patent Literature

PTL 1: U.S. Pat. No. 8,558,933

SUMMARY OF INVENTION

Technical Problem

However, in the system according to Patent Literature 1, when a plurality of patients are at a short distance from the display device, wireless communication between one sensor and the display device may be crossed with wireless communication between another sensor and the display device. Thus, in an anticipated situation, pieces of vital information measured by the sensors cannot be associated with the patients accurately respectively.

Therefore, an object of the invention is to provide a sensor which can support accurate association between vital information measured by a sensor and a patient.

Solution to Problem

In order to achieve the foregoing object, the sensor according to the invention includes: an acquisition unit which can acquire patient identification information so that a patient can be identified by the acquired patient identification information; a storage unit which stores the patient identification information acquired by the acquisition unit; a detection unit which can detect vital information of the patient; an association unit which associates the patient identification information stored in the storage unit, with the vital information; and a transmission unit which can transmit the vital information including the associated patient identification information, to an external device.

According to the configuration, vital information (a vital signal including the patient identification information) in a state in which the vital information and the patient identification information are linked with each other accurately can be received by the external device. Therefore, it is possible to support accurate association between the vital information and the patient. It is possible to, for example, display the vital information on a display screen etc. in a state in which the sensor measuring the vital information is accurately associated with the patient.

According to the sensor according to the invention, it is possible to support accurate association between the vital information measured by the sensor and the patient.

BRIEF DESCRIPTION OF DRAWINGS

FIG. 1 A schematic view showing a use example of sensors according to an embodiment of the invention.

FIG. 2 A block diagram for explaining functions of each of the sensors.

FIG. 3 A view showing an example of a message image displayed on a bedside monitor.

FIG. 4 A view showing an example of vital information displayed on the bedside monitor.

FIG. 5 A block diagram showing a modification of the sensor.

DESCRIPTION OF EMBODIMENTS

An embodiment of the invention will be described below by way of example with reference to the drawings. As shown in FIG. 1, sensors 1 according to the embodiment are attached on a patient in order to measure vital information such as an electrocardiogram, oxygen saturation ($SpO_2$), body temperature, respiration etc. FIG. 1 shows a state in which the patient hospitalized in a room of a hospital is attached with the sensors 1 and lies on a bed 41 so that the vital information of the patient can be measured by the sensors 1. In this example, a sensor 1a for measuring an electrocardiogram, a sensor 1b for measuring $SpO_2$, and a sensor 1c for measuring respiration are attached on the patient.

The sensors 1 are wireless sensors each of which has a short range wireless communication function. The sensors 1 are configured to be able to make wireless communication (e.g. Bluetooth (registered trademark)) with a bedside monitor 2 (an example of an external device) respectively.

The bedside monitor 2 is placed for each bed which is used by a patient hospitalized in the hospital room 100. The bedside monitor 2 has a display screen 21 so that the vital information of the patient received from the sensors 1 by wireless communication can be displayed on the display screen 21. In addition, the bedside monitor 2 is configured to be able to make communication with a nurse call system 3 placed in a nurse station 200. The bedside monitor 2 and the nurse call system 3 can be connected to each other, for example, through a wired cable or a wireless LAN (LAN: Local Area Network).

A patient information table in which information about all hospitalized patients has been recorded is saved in the nurse call system 3. For example, pieces of information including a patient ID (ID: identification), a patient's name, a patient's room number, a bed number, an attending doctor, an attending nurse, etc. are stored in association with the patients respectively in the patient information table. The nurse call system 3 can transmit the information of the patient information table to the bedside monitor 2 by wireless communication. In addition, the nurse call system 3 has a display screen 31 so that the vital information of the patient received from the bedside monitor 2 can be displayed on the display screen 31.

In addition, the sensors 1 are configured to be able to make wireless communication (e.g. Bluetooth) with a mobile communication terminal 4 (e.g. a smartphone, a tablet, or the like) held by a medical worker. Each of the sensors 1 has a unique sensor ID. The sensor ID may be inscribed on the sensor, for example, in a visually recognizable form.

For example, the mobile communication terminal 4 transmits patient identification information which can identify the patient, to the sensors 1 designated by the medical worker.

The patient identification information is unique patient information which is given from the hospital to each patient. For example, the patient identification information may include the patient ID, the patient's name, a patient's registration card number, etc. In addition, the mobile communication terminal 4 can communicate with the nurse call system 3 through the aforementioned wireless LAN and receive the information of the patient information table from the nurse call system 3.

An ID tag 51 is attached on a part (such as a wrist or an ankle) of the body of each hospitalized patient. Patient identification information which can identify the patient is stored in the ID tag 51. For example, the ID tag 51 is attached to a wristband. Alternatively, the patient identification information may be inscribed visually recognizably on the wristband. Incidentally, here, the term "inscribe" may mean to include a form in which, for example, the wristband has a liquid crystal screen so that the patient identification information such as the patient's name can be displayed on the liquid crystal screen in accordance with a button operation etc.

As shown in FIG. 2, each of the sensors 1 is provided with an acquisition unit 11 which can acquire patient identification information transmitted from the mobile communication terminal 4 by wireless communication. In addition, the sensor 1 is provided with a storage unit 12 which stores the patient identification information acquired by the acquisition unit 11.

The patient identification information stored in the storage unit 12 may be one kind of information or a plurality of kinds of information selected from the patient ID, the patient's name, the patient's registration card number, etc. The patient identification information stored in the storage unit 12 can be deleted. In addition, new patient identification information can be stored into the storage unit 12. For example, the patient identification information may be erased when a power supply of the sensor 1 is turned OFF or when the sensor 1 has not been used for a long time.

The sensor 1 is provided with a detection unit 13 which can detect vital information of the patient on which the sensor 1 is attached. In addition, the sensor 1 is provided with an association unit 14 which associates the patient identification information stored in the storage unit 12 with the vital information detected by the detection unit 13. Further, the sensor 1 is provided with a transmission unit 15 which can transmit the patient identification information-including vital information in which the patient identification information has been associated, to the bedside monitor 2 by wireless. Incidentally, although not shown, the sensor 1 is provided with a power supply portion (e.g. a coin cell battery) for supplying electric power to the respective portions of the sensor 1 and a power supply switch for activating the power supply portion.

Next, operation of the sensors 1 will be described with reference to FIGS. 1 to 4. First, as initial setting, a patient information table for a patient (e.g. called patient A) whose hospitalization has been determined is generated on the nurse call system 3. In addition, for example, a wristband to which an ID tag 51 is attached and on which the name (Ms. A) of the patient A is inscribed may be attached on a wrist of the patient A.

In order to measure vital information of the patient A, the medical worker goes to the hospital room 100 where the patient A is hospitalized. For example, by use of the smartphone 4, the medical worker associates the sensors 1 with the patient A. The sensors 1 are used for measuring the vital information of the patient A. The medical worker activates the power supplies of the sensors 1 to be used. In addition, for example, the medical worker activates a "sensor association" application which has been installed in the smartphone 4.

The smartphone 4 identifies sensors present within a wirelessly communicable area, and displays sensor IDs of the identified sensors on a screen of the smartphone 4. For example, the sensors 1 carried by the medical worker in order to measure the vital information of the patient A are identified, and the sensors ID of the sensors 1 are displayed on the screen of the smartphone 4.

The medical worker confirms the sensors ID inscribed on the carried sensors 1, and checks the sensors ID with the sensor IDs displayed on the screen of the smartphone 4. Then, the medical worker selects the sensors 1.

As a result of the selection, authentication succeeds between the smartphone 4 and the selected sensors 1 so that communication can be made between the smartphone 4 and the selected sensors 1. The smartphone 4 transmits a patient ID of the patient A, for example, to the authenticated sensors 1a to 1c. The vital information of the patient A is measured by the authenticated sensors 1a to 1c.

The patient ID transmitted from the smartphone 4 is acquired by the respective acquisition units 11 of the sensors 1a to 1c, and the acquired patient ID is stored in the respective storage units 12 of the sensors 1a to 1c.

The medical worker attaches the sensors 1a to 1c in which the patient ID of the patient A has been stored, on the patient A who is lying on the bed 41. Incidentally, the patient ID may be transmitted from the smartphone 4 to the sensors 1a to 1c and the transmitted patient ID may be stored into the storage units 12 of the sensors 1a to 1c, after the sensors 1a to 1c have been attached on the patient A.

When the sensors 1a to 1c are attached on the patient A, the detection units 13 of the sensors 1a to 1c start detecting pieces of vital information respectively. The association units 14 of the sensors 1a to 1c associate the patient ID of the patient A stored in the storage units 12, with the pieces of vital information detected by the detection units 13, respectively.

The transmission units 15 of the sensors 1a to 1c respectively transmit pieces of patient ID-including vital information in which the patient ID has been associated, to the bedside monitor 2 by wireless. For example, the transmission unit 15 of the sensor 1a writes the patient ID into a header area, and then transmits the piece of patient ID-including vital information in which electrocardiogram data are written into a data region following the latter part of the header area, by wireless.

Upon reception of the pieces of patient ID-including vital information, the bedside monitor 2 refers to the patient information table held by the nurse call system 3 of the nurse station 200 to specify the name ("Ms. A") of the patient A associated with the patient ID. The bedside monitor 2 displays a message indicating "Ms. A's vital information has been received", as a pop-up screen 22 on the display screen 21, for example, as shown in FIG. 3.

The medical worker confirms display contents of the pop-up screen 22 and confirms that Ms. A is the patient herself. Then, the medical worker touches the pop-up screen 22.

The bedside monitor 2 cancels the pop-up screen 22, and displays the pieces of vital information of the patient A, for example, together with the name ("Ms. A") of the patient A, on the display screen 21, as shown in FIG. 4.

By an operation on the nurse call system 3, each of the pieces of vital information of the patient A displayed on the aforementioned bedside monitor 2 can be transmitted from the bedside monitor 2 to the nurse call system 3 by wireless, and displayed on the display screen 31 of the nurse call system 3.

The measurement of the pieces of vital information of the patient A is completed. Then, the sensors $1a$ to $1c$ are removed from the patient A. When, for example, the power supplies of the sensors $1a$ to $1c$ are turned off, the patient ID of the patient A which has been stored in the respective storage units 12 is erased. Thus, the sensors $1a$ to $1c$ can be used for measurement of new vital information, such as measurement on another patient.

In a background-art medical device for measuring patient information using wireless sensors, for example, assume that sensors $a1$ to $a3$ (not shown) are attached on a patient A and sensors $b1$ to $b3$ (not shown) are attached on a patient B. In this case, the medical device which has received information from the sensors cannot automatically associate information of the sensor $a1$ with information of the patient A. In this case, for example, device numbers belonging to the sensors can be associated with pieces of information of the patients respectively but there is a possibility that a human error may occur in the association work. In addition, for example, it may be also considered that a patient ID can be manually inputted in accordance with each sensor and associated therewith. Similarly to the aforementioned case, there is however a possibility that a human error may occur. In addition, whenever the patient is replaced by another person, work for deleting the associated patient ID is required to thereby result in an increase in workload.

To solve the problems, according to the sensors 1 according to the embodiment, the patient ID of the patent A is transmitted to the sensors $1a$ to $1c$ through the smartphone 4 of the medical worker when, for example, the pieces of vital information of the patient A are measured. The sensors $1a$ to $1c$ are prepared for measuring the pieces of vital information of the patient A. In addition, the transmitted patient ID of the patient A is stored into the respective storage units 12 of the sensors $1a$ to $1c$. Therefore, the sensors $1a$ to $1c$ can accurately associate the patient ID of the patient A stored in the storage units 12, with the pieces of vital information of the patient A detected by the detection units 13, respectively. Accordingly, the bedside monitor 2 can receive a signal of the patient ID-including vital information in which the detected pieces of vital information of the patient A are accurately associated with the patient ID of the patient A. Thus, the bedside monitor 2 can display the signal of the patient ID-including vital information on the display screen 21 etc. in a state in which the sensors $1a$ to $1c$ measuring the pieces of vital information are accurately associated with the patient A ("Ms. A").

In addition, the smart phone 4 can be used to store the patient ID into the storage units 12 of the sensors $1a$ to $1c$. Accordingly, user-friendliness for the medical worker is excellent. In addition, after the patient ID has been deleted from the storage units 12 of the sensors $1a$ to $1c$, a patent ID of a new patient can be stored into the storage units 12 of the sensors $1a$ to $1c$. Accordingly, the sensors $1a$ to $1c$ can be reused for another patient.

<Modification 1>

As shown in FIG. 5, an acquisition unit 11 of each sensor 1 may be constituted by a reader unit 11A which can read patient identification information of a patient A, for example, from an ID tag 51 attached to a wristband of the patient A. For example, the reader unit 11A has a signal processing portion which makes communication with the ID tag 51. The signal processing portion sends a radio wave to the ID tag 51 and receives the patient identification information sent back from the ID tag 51. In this manner, the reader unit 11A can read the patient identification information.

A medical worker can allow communication between sensors $1a$ to $1c$ attached on the patient A and the ID tag 51 of the patient A, so that the patient identification information of the patient A stored in the ID tag 51 can be read by the respective reader units 11A of the sensors $1a$ to $1c$. The patient identification information read by the respective reader units 11A is stored into the respective storage units 12 of the sensors $1a$ to $1c$.

The medical worker attaches the sensors $1a$ to $1c$ in which the aforementioned patient identification information of the patient A has been stored, onto the patient A who is lying on a bed 41. Operation of each sensor 1 attached on the patient is similar to that in the aforementioned embodiment.

According to such a configuration, for example, the patient identification information on the wristband attached by the patient is read by the reader units 11A of the sensors $1a$ to $1c$. Thus, the patient identification information can be stored into the respective storage units 12 of the sensors $1a$ to $1c$. Therefore, user-friendliness is excellent because the medical worker does not have to operate a mobile communication terminal. In addition, the sensors $1a$ to $1c$ can be further accurately associated with the patient A.

<Modification 2>

The configuration of each sensor 1 according to the aforementioned embodiment may be modified so that the patient ID stored in the storage unit 12 cannot be deleted. According to the modified configuration, for example, the sensor 1 in which the patient ID of the patient A has been stored for measuring vital information of the patient A cannot be used on another patient. Therefore, the sensor 1 can be made disposable to reduce the risk of using the sensor 1 on another patient by mistake.

Incidentally, the invention is not limited to the aforementioned embodiment. Any modification, improvement, etc. can be made on the invention desirably and suitably. Besides, the materials, shapes, dimensions, numerical values, forms, numbers, arrangement places etc. of the respective constituent elements in the aforementioned embodiment are not limited but may be set desirably as long as the invention can be achieved.

For example, assume that the hospital room is a large room where a plurality of patients are hospitalized, and the plurality of patients on which sensors are attached exist within the wirelessly communicable area of the smartphone 4. In this case, all sensor IDs of the sensors 1 attached on the patients are displayed on the screen of the smartphone 4. In this case, from the sensor IDs of the sensors 1 attached on the patients, that is, the sensor IDs displayed on the screen of the smartphone 4, the medical worker may select sensors ID of sensors 1 intended to measure vital information of the patient A.

The present application is based on Japanese Patent Application No. 2016-127896 filed on Jun. 28, 2016, the contents of which are hereby incorporated by reference.

1 ($1a$ to $1c$): sensor, 2: bedside monitor (example of external device), 3: nurse call system, 4: mobile communication terminal, 11: acquisition unit, 11A: reader unit, 12: storage unit, 13: detection unit, 14: association unit, 15: transmission unit, 21, 31: display screen, 51: ID tag, 100: hospital room, 200: nurse station

The invention claimed is:

1. A sensor system comprising:
a plurality of reusable and/or disposable sensors configured to be worn by a patient, each of the plurality of sensors having a unique sensor identifier (ID) and displaying the sensor ID in a visually recognizable form;
a mobile communication terminal operated by a medical worker and configured to:
  identify all sensors, from the plurality of sensors, that are within a wirelessly communicable area of the mobile communication terminal;
  display the sensor IDs for each of the identified sensors such that the medical worker can match the sensor ID of a carried or worn sensor with an identified sensor ID displayed on the mobile terminal, thereby confirming the identity of the carried or worn sensor;
  transmit patient identification information of the patient to the confirmed sensor upon selection of the confirmed sensor by the medical worker, so that the patient can be identified by the patient identification information; and
a bedside monitor,
wherein each of the plurality of sensors comprises:
  an acquisition unit configured to acquire the patient identification information from the mobile communication terminal or an identification tag worn by a patient;
  a storage unit configured to store the patient identification information acquired by the acquisition unit;
  a detection unit configured to detect vital information of the patient;
  an association unit configured to associate the patient identification information stored in the storage unit, with the vital information; and
  a transmission unit configured to transmit, in a transmission signal, the vital information and the associated patient identification information to the bedside monitor, and
wherein the bedside monitor is configured to selectively display the received vital information from the sensors storing the same patient identification information,
wherein the reusable sensors are configured to delete the stored patient identification information from the storage when the reusable sensor is turned OFF, and
wherein the patient identification information stored in the storage unit cannot be deleted in the disposable sensors.

2. The sensor system according to claim 1, wherein the mobile communication terminal is further configured to receive the patient identification information from an external database.

3. The sensor system according to claim 1, wherein the bedside monitor is further configured to transmit the received vital information to an external database, the external database already storing the patient identification information associated with the transmitted vital information.

4. The sensor system according to claim 1, wherein the bedside monitor is further configured to:
  communicate with an external database and thereby identify a name of the patient based on the patient identification information, and
  display the identified name with the received vital information.

5. The sensor system according to claim 4, wherein the bedside monitor is configured to:
  display the identified patient name in a pop-up screen, and
  upon confirmation by the medical worker that the identified patient name is correct, display the associated received vital information.

6. The sensory system according to claim 1, wherein the mobile communication terminal is further configured to selectively display the sensor IDs of the sensors storing the same patient identification information.

7. The sensor system according to claim 1, wherein the associated patient identification information is in a header area of the transmission signal and the vital information is in a data region following the header area of the transmission signal.

8. A sensor having unique sensor identifier (ID), the sensor comprising:
an acquisition unit configured to acquire patient identification information from a mobile communication terminal operated by a medical worker during a sensor confirmation process, the mobile communication terminal being within a wirelessly communicable area of the sensor;
a storage unit configured to store the patient identification information acquired by the acquisition unit;
a detection unit configured to detect vital information of the patient;
an association unit configured to associate the patient identification information stored in the storage unit, with the vital information; and
a transmission unit configured to transmit the vital information and the associated patient identification information to an external bedside monitor, the bedside monitor being configured to selectively display vital information from the sensor, and additional sensors, storing the same patient identification information,
wherein the sensor ID is provided in a visually recognizable form on the sensor, such that the sensor is verifiable by the medical worker by comparing the sensor ID on the sensor with a display of the sensor ID on the mobile communication terminal during the sensor confirmation process,
wherein when the sensor is reusable, the storage unit is configured to delete the stored patient identification information when the sensor is turned OFF, and
wherein when the sensor is disposable, the patient identification information stored in the storage unit cannot be deleted.

* * * * *